United States Patent
Tanner et al.

(10) Patent No.: US 11,667,885 B2
(45) Date of Patent: Jun. 6, 2023

(54) METHOD OF CULTIVATING ALGAE

(71) Applicants: NESTE OYJ, Espoo (FI); SUOMEN YMPÄRISTÖKESKUS SYKE, Helsinki (FI)

(72) Inventors: Reijo Tanner, Hikiä (FI); Jukka Seppälä, Jokela (FI); Timo Tamminen, Espoo (FI); Kristian Spilling, Helsinki (FI); Pasi Ylöstalo, Jokela (FI); Pauliina Uronen, Kerava (FI)

(73) Assignees: NESTE OYJ, Espoo (FI); SUOMEN YMPÄRISTÖKESKUS SYKE, Helsinki (FI)

( * ) Notice: Subject to any disclaimer, the term of this patent is extended or adjusted under 35 U.S.C. 154(b) by 115 days.

(21) Appl. No.: 15/525,206

(22) PCT Filed: Nov. 4, 2015

(86) PCT No.: PCT/FI2015/050760
§ 371 (c)(1),
(2) Date: May 8, 2017

(87) PCT Pub. No.: WO2016/071570
PCT Pub. Date: May 12, 2016

(65) Prior Publication Data
US 2017/0335274 A1 Nov. 23, 2017

(30) Foreign Application Priority Data
Nov. 7, 2014 (EP) .................. 14192180

(51) Int. Cl.
*C12N 1/12* (2006.01)
*C12P 7/64* (2006.01)
*C12N 1/38* (2006.01)
*C12P 7/6463* (2022.01)

(52) U.S. Cl.
CPC ............ *C12N 1/12* (2013.01); *C12N 1/38* (2013.01); *C12P 7/6463* (2013.01)

(58) Field of Classification Search
CPC ............ C12N 1/12; C12N 1/38; C12P 7/6463
See application file for complete search history.

(56) References Cited

U.S. PATENT DOCUMENTS

| 2012/0077253 A1 | 3/2012 | Burkhead et al. |
| 2014/0051131 A1 | 2/2014 | Dodd et al. |
| 2014/0242641 A1 | 8/2014 | Tamis et al. |

FOREIGN PATENT DOCUMENTS

| CN | 103052715 A | 4/2013 |
| CN | 103352006 A | 10/2013 |
| CN | 103642694 A | 3/2014 |
| CN | 104195189 A | 12/2014 |
| WO | 2010/063256 A2 | 6/2010 |
| WO | 2010/063256 A3 | 6/2010 |
| WO | 2012/006302 A1 | 1/2012 |
| WO | 2012006302 A1 | 1/2012 |
| WO | 2012/016208 A1 | 2/2012 |
| WO | 2012/101459 A2 | 8/2012 |
| WO | 2013/012329 A1 | 1/2013 |

OTHER PUBLICATIONS

Boussiba et al. Astaxanthin accumulation in the Green algae *Haematococcus pluvialis.*, Plant Cell Physiol. (1991), 32(7): 1077-1082, see PTO892).*
Seyfabadi et al. Protein, fatty acid, and pigment content of Chlorella vulgaris under different light regimes. J Appl Phycol (2011), 23: 721-726.*
International Search Report (PCT/ISA/210) dated Mar. 7, 2016, by the Finnish Patent Office as the International Searching Authority for International Application No. PCT/FI2015/050760.
Written Opinion (PCT/ISA/237) dated Mar. 7, 2016, by the Finnish Patent Office as the International Searching Authority for International Application No. PCT/FI2015/050760.
European Search Report (EPO Form 1507N) dated May 6, 2015.
Copyright Notice dated Nov. 4, 2015 regarding the Grewe et al., Rosen et al., Klok et al., Gwak et al., and Ho et al. articles as well as CN 104195189.
Grewe C. et al., "Time-and media-dependent secondary carotenoid accumulation in Haematococcus pluvialis", Biotechnology Journal, Oct. 2008, vol. 3, No. 9-10, pp. 1232-1244.
Rosen, B. et al., "Physiological and ultrastructural responses of Cyclotella meneghiniana (Bacillariophyta) to light intensity and nutrient limitation", Journal of Phycology, 1984, vol. 20, No. 2, pp. 173-183.
Klok, A. J. et al., "Simultaneous growth and neutral lipid accumulation in microalgae", Bioresource Technology, 2013, vol. 134, pp. 233-243.
Gwak, Y. et al., "Comparative analyses of lipidomes and transcriptomes reveal a concerted action of multiple defensive systems agains photooxidative stress in Haematococcus pluvialis", Journal of Experimental Botany, May 2014, vol. 65, No. 15, pp. 4317-4334.
Ho et al., "Dynamic metabolic profiling of the marine microalga *Chlamydomonas* sp. JSC4 and enhancing its oil production by optimizing light intensity", Biotechnology for Biofuels, Mar. 2015, vol. 8:48, 17 pages.
Mujtaba et al., "Lipid production by Chlorella vulgaris after a shift from nutrient-rich to nitrogen starvation conditions", Bioresource Technology, vol. 123, Jul. 27, 2012, pp. 279-283.
Saha et al., "Effect of macro- and micro-nutrient limitation on superoxide dismutase activities and carotenoid levels in microalga *Dunaliella salina* CCAP 19/18", Bioresource Technology, vol. 147, Aug. 9, 2013, pp. 23-28.
Aikawa et al., "Synergistic enhancement of glycogen production inby optimization of light intensity and nitrate supply", Bioresource Technology, vol. 108, Jan. 9, 2012, pp. 211-215.

(Continued)

*Primary Examiner* — Iqbal H Chowdhury
(74) *Attorney, Agent, or Firm* — Buchanan Ingersoll & Rooney PC

(57) ABSTRACT

The present description is related to the field of cultivating algae. It introduces a method of cultivating algae by depleting the culture of an inorganic nutrient and exposing the alga to high intensity light to obtain algal cell mass having enriched lipid content and reduced chlorophyll content.

13 Claims, 12 Drawing Sheets

(56) References Cited

OTHER PUBLICATIONS

Tran et al., "Proteomics analysis of proteins in green alga *Haematococcus lacustris* (Chlorophyceae) expressed under combined stress of nitrogen starvation and high irradiance", Enzyme and Microbial Technology, Stoneham, MA, US, vol. 45, No. 4, Oct. 7, 2009, pp. 241-246.

Kang et al., "Fed-batch culture of astaxanthin-rich Haematococcus pluvialis by exponential nutrient feeding and stepwise light supplementation", Bioprocess and Biosystems Engineering, Springer, Berlin, DE, vol. 33, No. 1, Aug. 7, 2009, pp. 133-139.

Grama et al., "Induction of canthaxanthin production in aDactyloccusmicroalga isolated from the Algerian Sahara", Bioresource Technology, vol. 151, Nov. 1, 2013, pp. 297-305.

Pal et al., "The effect of light, salinity, and nitrogen availability on lipid production by *Nannochloropsis* sp.", Applied Microbiology and Biotechnology, vol. 90, No. 4, Mar. 23, 2011, pp. 1429-1441.

Sharma et al., "High lipid induction in microalgae for biodiesel production", Energies, Molecular Diversity Preservation International (MDPI), AG, Switzerland, vol. 5, May 18, 2012, pp. 1532-1553.

Juneja et al., "Effects of Environmental Factors and Nutrient Availability on the Biochemical Composition of Algae for Biofuels Productions: A Review", Energies, vol. 6, No. 9, Sep. 3, 2013, pp. 4607-4638.

Liu et al., "Effects of Light Intensity on the Growth and Lipid Accumulation of *Microalga* Sp. 11-1 Under Nitrogen Limitation", Applied Biochemistry and Biotechnology; Part A: Enzyme Engineering and Biotechnology, Humana Press Inc., New York, vol. 166, No. 8, Mar. 14, 2012, pp. 2127-2137.

*Kaixian et al., "Light and nitrogen deficiency effects on the growth and composition of Phaeodactylum tricornutum", Applied Biochemistry and Biotechnology; Part A: Enzyme Engineering and Biotechnology, Humana Press Inc., New York, vol. 38, No. 1-2, 1993, pp. 93-103.

R. Geider, et al., "Redfield revisited: variability of C:N:P in marine microalgae and its biochemical basis", European Journal of Phycology, 2002, pp. 1-17, vol. 37, No. 1.

Office Action dated Dec. 16, 2019, by the Brazilian Patent Office in corresponding Brazilian Patent Application No. BR112017009306-5, and a partial English Translation of the Office Action. (6 pages).

First Office Action dated Feb. 28, 2020, by the Chinese Patent Office in corresponding Chinese Patent Application No. 201580060411.2, and an English Translation of the Office Action. (14 pages).

* cited by examiner $$\mu = \mu\_max(1-\exp^{-(1/K\_e)*E})$$

METHOD OF CULTIVATING ALGAE

FIELD OF THE INVENTION

The present description is related to the field of lipid production from algae. It provides a novel method which can be used to produce algae and algal biomass with high lipid content and low chlorophyll content. The algal biomass produced by the present method is particularly useful for cultivating algae for biofuel production or other refining products.

BACKGROUND

Algae are seen as one of the most promising biomass and biofuel raw material producers in our economy worldwide. The areal production potential of algae oil is estimated to be among the best ones in the world: realistic estimations show that algae oil could be produced in large scale with a 20-30 t/ha/year yield. This can be compared to other vegetable oil productivities which range from less than 1 to up to 6 t/ha/year (e.g. rapeseed oil, palm oil). In addition, algae cultivations can be located on unfertile, low quality land areas. Besides land use benefits, the greenhouse gas reduction potential is high: Calculations show that emissions from algae oil based biofuels can be less than 70-80% compared to fossil fuels. These benefits are important to recognize as the biofuel industry constantly aims at more sustainable raw materials and land use, as well as to finding new methods to reduce greenhouse emissions. Consequently, all new raw material options have to be evaluated carefully before entering in large scale production.

Although algae are well understood as a potential and environment friendly option for biofuel raw material production, until now the capital and operational expenses have been too high for the low value fuel markets. Therefore all process steps need new innovations which realize the cut in the total capital need. Capital expenses are mainly driven by the oil productivity level. A deeper analysis in the term "oil productivity" shows that it consists of two parts: biomass production and lipid production. A trade-off between these properties is well documented in scientific literature, and oil productivity can be improved by careful strain selection, by choosing the right cultivation protocols, and by optimizing the harvesting time. Methods that increase the oil productivity are of highest importance in order to decrease the capital investments.

When oil is extracted from the algae biomass, cellular chlorophylls tend to enter the oil fraction and the concentration of chlorophyll can be as high as 1-3% in the final oil. In the vegetable oil processing chlorophyll concentrations of already 30-100 ppm are considered high and have been seen to cause problems both in the pre-treatment and in the catalytic processing of the oil. Chlorophyll cannot be removed from the oil by degumming and bleaching is uneconomical even in vegetable oil processing since it demands an increased amount of bleaching clay leading to substantial oil losses. In the oil refining step, chlorophylls are strongly adsorbed at the entrance of the catalyst's pores, which leads to slower hydrogenation rates. Therefore it has been difficult to develop economically feasible processes for algal lipid production which produce sufficiently large amount of lipids in a short time.

Previous methods to increase lipid content in algae have often used nitrogen limitation, which has also been reported to reduce cellular chlorophyll levels. Lipid accumulation takes place during stress conditions when cell division and carbon fixation are in imbalance, and typically nitrogen limitation is considered as a main cause for lipid accumulation. When nitrogen limitation starts, no new nitrogen-containing proteins can be metabolized and the production of other compounds, e.g. lipids and hydrocarbons increases.

Photoacclimation is a universally noted phenomenon, where photosynthetic pigments are decreased in high light to balance the amount of light harvested versus the amount of energy that can be used by the cells. Traditionally algae research has focused on exploring growth rates in different light levels and on estimation of photosynthetic efficiency in different light conditions.

High lipid productivity in algae has thus far been reached by a two-step cultivation process: first biomass comprising algae is produced, and then cells are driven to deficiency of some mineral (nitrogen, phosphorus or silica). During this starvation stage cells start to storage lipids or starch in their cells, because their ability to produce normal biomass is limited.

The starvation stage is not easy to reach in cultivation with high algal biomass and it takes a long time, from many days to weeks. It has been evaluated that the fattening stage, during which lipids are accumulated, can take several days to weeks from the beginning of starvation in algae cultivations which is too long for cultivating algae for fuel production. Prior methods have not been successful in moving algae cells quickly enough from the growth phase to the oil production phase to provide lipid rich algae biomass for biofuel production.

WO2012/006302 discloses a method of cultivating microalgae *Chlorococcum pamirum* and increasing oil production. Oil accumulation was induced by nitrogen or phosphorus deficient medium, or by continuously illuminating the microalgae cells during the entire cultivation time with light having intensity higher than at least 200 μmol m$^{-2}$ (p. 5-6). The algal oil content could be increased with these methods within a week to ten days. Combining nitrogen deficiency with constant high intensity light illumination during the whole cultivation stage further increased the speed of oil accumulation but not the final oil content (Example 3).

US2012/0077253 discloses a method of cultivating algae in a photobioreactor with optimal and constant growth rate for longer periods of time [0054-0056]. The algal cell mass is monitored and controlled during culturing to keep the ratio of emitted photons to cell density at a defined range by increasing or decreasing light exposure and/or algal mass. The method provides optimal oil production only by culturing within the ideal specific light irradiation range of the algae strain and by avoiding high spikes in light irradiance [0066]. During growth phase, the desired level of specific irradiation must be maintained [0067].

Lipid accumulation is an important step in culturing algae biomass, since the storage lipids are usually neutral lipids, such as triglycerides, which can readily be used as feedstock in biofuel processing. Structural lipids, in contrast, are mainly polar lipids, such as phospholipids and glycolipids. Therefore during starvation the absolute amount of cellular neutral lipids increases and the share of neutral vs. polar lipids increases.

It is thus an object of the present invention to solve or alleviate at least some of the above problems of prior art.

SUMMARY OF THE INVENTION

The present inventors have surprisingly found that chlorophyll amount can be decreased and lipid content increased in algal cells by depleting the cells of nutrient, especially nitrogen, to a level causing nutrient stress, and exposing the cells essentially at the same time to high intensity light. With the present method the change to lipid accumulation phase is achieved much faster than with conventional methods, which shortens the total time required for cultivation and lipid production, and makes the method particularly useful and economically viable for producing lipid-enriched algae for biofuel production.

According to the first aspect of the invention there is provided a method of producing algal cells, comprising the steps of:
 a. cultivating algal cells in culture conditions and in an amount of light that support growth;
 b. depleting the algal cells of at least one inorganic nutrient; and
 c. exposing the algal cells continuously to an amount of light which is higher than in step a.;
wherein step b. and step c. are started essentially at the same time.

The method has an advantage of faster switch of the cultivated algal cells from biomass to lipid accumulation phase. Accordingly, the present method is useful to produce algal biomass for biofuel production.

Another advantage is that the lipid-to-chlorophyll ratio of the algal cells increased remarkably. The cells which had encountered the innovative nutrient starvation and high light treatment moved rapidly, even within hours, from growth stage to lipid production stage, they contained 140% more lipids than reached with traditionally cultivation methods (but normally during days-weeks) and a lower chlorophyll content which improved their lipid:chlorophyll ratio 17-fold.

According to the second aspect of the invention there is provided an alga produced using the above method.

The alga and the algal mass comprising algal cells according to the invention contain more lipids and less chlorophyll than the corresponding algal cells cultivated using prior methods known to date.

The alga produced according to the above method finds particular use in biofuel production. Biomass comprising algal cells produced with the present method can be produced in a shorter cultivation time, and the algal cells are enriched in lipids and contain less chlorophyll than what can be achieved with prior art methods.

According to the third aspect of the invention there is provided a lipid extract obtainable by extracting lipids from algae produced using the present method. The lipid extraction may be carried out using any method known in the art to extract lipids from algal cells.

According to the fourth aspect of the invention there is provided biofuel obtainable by converting lipids from the alga produced using the method above and/or the above lipid extract into a biofuel.

According to the fifth aspect of the invention there is provided use of the present alga and/or the present lipid extract in fuel production. Due to increased lipid content and decreased chlorophyll content, as well as the faster switch from growth phase to lipid production phase, the use is particularly advantageous as it shortens the overall processing time in fuel production and simplifies production by decreasing the need for removing chlorophyll.

According to the sixth aspect there is provided a method of producing renewable biofuel comprising: culturing algal cells according to the present method, isolating lipid components from the cultured algae; and subjecting the isolated lipid components to chemical reactions to generate hydrocarbons or alkylesters of fatty acids whereby renewable biofuel is produced.

According to the seventh aspect there is provided a method of increasing neutral lipid to chlorophyll ratio in algal cells comprising
 a. cultivating algal cells in culture conditions and in an amount of light, that support growth;
 b. depleting the algal cells of at least one inorganic nutrient; and
 c. exposing the algal cells continuously to an amount of light which is higher than in step a.;
wherein step b. and step c. are started essentially at the same time.

According to the eighth aspect there is provided use of the lipid extract to reduce catalyst blocking in a biofuel conversion unit, in which algae oil is converted to biofuel components. The present lipid extract is also useful to improve catalytic conversion of lipids into biofuel. The present lipid extract is particularly useful in biofuel production by improving the performance of catalysts needed in conversion of algal lipids into biofuel because of lower chlorophyll content and the high neutral lipid content of the algal lipids produced according to the present method.

Without limiting to the above advantages, the present method, products and uses are improved over what can be accomplished with prior cultivation methods because the present method changes the algal cells more rapidly from growth stage to lipid production stage and yields algae with increased lipid to chlorophyll ratio.

Different embodiments of the present invention will be illustrated or have been illustrated only in connection with some aspects of the invention. A skilled person appreciates that any embodiment of an aspect of the invention may apply to the same aspect of the invention or other aspects of the invention.

DETAILED DESCRIPTION

Figure 1:
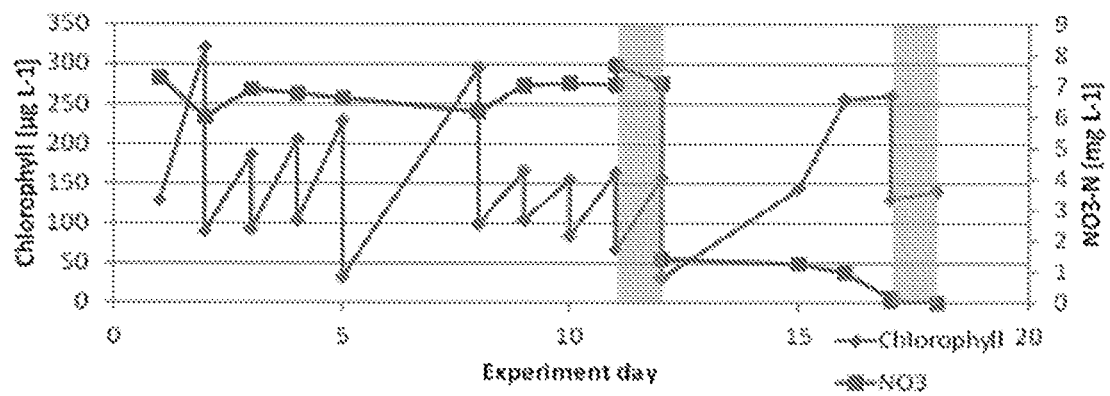
FIG. 1 discloses development of Chlorophyll and nitrate ($NO_3$—N) concentrations during first light experiment. Daily variations are due to dilutions with fresh media. At the days 12 and 17, the culture was diluted with nitrogen free media, causing a drop in $NO_3$ concentrations. Light-shift experimental periods when subsamples have been taken for different light treatments are shown in grey bars. Chlorophyll is either measured analytically or estimated from fluorescence. Nitrate is measured at days 11-15.

The culture conditions that support growth in the present methods are culture conditions in which the algal cells grow and divide. Any growth medium typically used in algal cultivation may be used. The amount of light supporting growth is the intensity of light received by an algal cell which is sufficient to allow the cell to grow and divide in the selected conditions supporting algal cell growth and without inhibiting accumulation of algal cell mass.

Depletion of an inorganic nutrient may be accomplished by not supplementing the growth medium with the inorganic nutrient after the desired biomass concentration has been achieved, whereby the inorganic nutrient is consumed by the algal cells. Alternatively, cells can be harvested by centrifugation, or by other means suitable for separating viable cells from the growth medium, and transferred to a new growth medium depleted with at least one inorganic nutrient. However, any suitable method may be used to reach a situation where the cells are located in a medium without at least one inorganic nutrient.

In certain embodiments of the present invention the level to which the inorganic nutrient is depleted is sufficiently low to induce nutrient stress in algal cells. The depleted inorganic nutrient can be nitrogen and the level inducing nutrient stress may be DIN=0 (DIN=dissolved inorganic nitrogen), which may be determined by methods known in the art. The level may be as low as the detection level of the inorganic nitrogen, or DIN=0.

Exposing the algal cells in step c. continuously to an amount of light which is higher than used to cultivate cells in step a. can be performed using any light source which is able to provide enough light to achieve the objectives of the invention.

The step b. is started essentially at the same time with the step c. Preferably, the light exposure step c. is started at a time point that occurs during one cell division before and one cell division after the time when a dissolved inorganic nutrient is under the detection limit in the cell culturing medium. In an embodiment the light exposure is started just before the majority of the algal cells have divided for the last time before inorganic nutrient depletion. As is well known in the art, the time period for one cell division may vary depending on the culturing conditions and the time period for one cell division can be determined according to methods known in the art. Accordingly, the proper time point to start the light treatment of step c. can easily be determined by measuring the concentration of the inorganic nutrient and the time period for cell division activity. Thus, a skilled person is able to start the steps b. and c. essentially at the same time, i.e. not sooner than and not later than one cell division from the time point when the amount of inorganic nutrient falls, or is estimated to fall, below a detection limit.

The present method provides algal cell biomass having high lipid content and low chlorophyll content. Such biomass is advantageous in biofuel production, because it reduces the need to remove chlorophyll from the biomass and provides more lipid to be converted to a biofuel.

In an embodiment the above method is for increasing neutral lipid to chlorophyll ratio in an alga or in the lipid extract produced from the alga.

In an example embodiment the inorganic nutrient which is depleted in the present methods may be nitrogen, phosphorus or silica. Depletion of inorganic nitrogen is preferred because it is a commonly used and very efficient method to induce lipid accumulation in algae cells. However, other nutrients, such as phosphorus or silica, can also be used for inducing lipid accumulation.

In an example embodiment, the above step c. is continued for at least three hours. Step c may also be carried out for longer than three hours, such as 3.5 h, 4 h, 4.5 h, 6 h, 6.5 h, 7 h, 7.5 h, 8 h, 9 h, 9.5 h, 10 h, 10.5 h, 11 h, 11.5 h, 12 h, or longer. However, three hours is sufficient to increase, compared to control alga, lipid content and decrease chlorophyll content to levels that make algae suitable for biofuel production.

In an example embodiment the algal cells are collected 12 h or more after induction of nutrient depletion. In a preferred example embodiment the algal cells are collected 12, 13, 14, 15, 16, 17, 18, 19, 20, 21, 22, 23, 24, 25, 26, 27, 28, 29, 30, 31, 32, 33, 34, 35, or 36 h after induction of nutrient depletion.

In another example embodiment the algal cells are collected 1, 2, 3, 4, 5, 6 or 7 days after inducing nutrient depletion.

In an example embodiment the amount of light to which the algal cell is exposed in step c. corresponds to or exceeds $E_k$, i.e. the amount of irradiance at which photosynthesis ceases to be light-limited. The light saturation parameter $E_k$ is given as $E_k=\mu_{max}/alpha$, wherein alpha is the initial slope between growth rate and irradiance relationship for a given alga. At some irradiance level, growth rates reach a plateau. The light-saturated growth rate is denoted $\mu_{max}$. A skilled person is readily able to determine the $E_k$ of any algal species using methods known in the art. In an embodiment step c. is carried out by exposing the alga to an amount of light which has an intensity corresponding to or exceeding the light level of $E_k$, $1.5 \times E_k$, $2 \times E_k$ or $3 \times E_k$ of said alga. Preferably the amount of light has in step c. an intensity equal to or below than needed at $\mu_{max}$.

In an example embodiment the amount of light in step c. may be at least 100, 110, 120, 130, 140, 150, 160, 170, 180, 190, 200, 210, 220, 230, 240, 250, 300, 350, 400, 450, 500, 550, 600, 560, 600, 650, 700, 750, 800, 850, 900, 950, 900, 950, 1000, 1100, 1200, 1300, 1400, 1500, 1550, 1600, 1650, 1700, 1750, 1800, 1850, 1900, 1950 or 2000 μmol photons $m^{-2} s^{-1}$.

In an embodiment in the step a. the amount of light that the cell is exposed to has an intensity lower than $E_k$ of said alga.

In an example embodiment, the cultivation is done using a day-night light cycle. Examples of day-night light cycles according to the invention are 12 h light period and 12 h dark period (12-12 cycle), 11-13 cycle, 8-16 cycle, or any naturally occurring light-dark period, or a cycle mimicking the normal periodicity between day and night. The light exposure period in step c. is given and included in the light period to keep the total length of the cycle unchanged during the method.

In an example embodiment, the high light treatment is given at the start of the day period and the amount of light is kept essentially constant during the rest of the day period. Preferably, the amount of light that the cell receives is kept at an essentially constant high level during the light treatment and at an essentially constant lower level during the rest of the day period.

In an example embodiment, the above step c. is repeated at the start of each successive day period as long as the method is continued and until harvesting the algal biomass.

Algal cells are preferably started to be exposed to the light treatment when they have not yet entered the stationary growth phase. However, lipid content can be increased and chlorophyll content decreased with the present method also in the case when the cells have reached stationary phase. In either case the light treatment is not given until the nutritional depletion has begun.

EXAMPLES

The following examples are provided to illustrate various aspects of the present invention. They are not intended to limit the invention, which is defined by the accompanying claims.

Light and starvation effects in algal cells were studied both in actively growing algae cells (exponential growth) and with algae cells that had reached stationary phase. Four light levels were tested, namely 60, 200, 600 and 1700 µmol photons $m^{-2}$ $s^{-1}$, which represented the level of normal sun light penetrating algae cultivations to 2.2; 1.4; 0.7 and 0 cm depths (assuming algae biomass concentrations as 1 g DW $L^{-1}$, Chlorophyll content of 1% of DW). Basic light level 60 µmol photons $m^{-2}$ $s^{-1}$ was the reference control value to which the impact of increased light was compared. Because the level 200 photons $m^{-2}$ $s^{-1}$ was high enough to see clear effects in algae cell physiology and behavior as lipid producers, we could identify the relation of the minimum light level that lead to strong impacts and the species-specific growth-irradiance relationship. Separate experiments were run with continuous light dosing and with pulses in second or minute scale. Best results, i.e. the fastest change to lipid accumulation phase and highest lipid:chlorophyll ratio of the algal cells, were obtained when extra light was given continuously at least for three hours.

Algae biomass was produced with maximum specific growth rate, and the nitrogen level was carefully monitored so that the photoactivation experiment was started immediately when inorganic nitrogen was under detection limit in the cultivation medium. The experimental cell density was intentionally low in order to avoid cellular shading and to provide the same light conditions to all the cells during the whole cultivation time.

The algae produced using the present method had high lipid content and lower chlorophyll content than obtained in the reference conditions. The present algae is especially useful when used for biofuel production because, in addition to high lipid content, the algae cells contain less chlorophyll which causes problems in lipid production and is difficult to remove from the algae biomass.

Example 1

Figure 2:
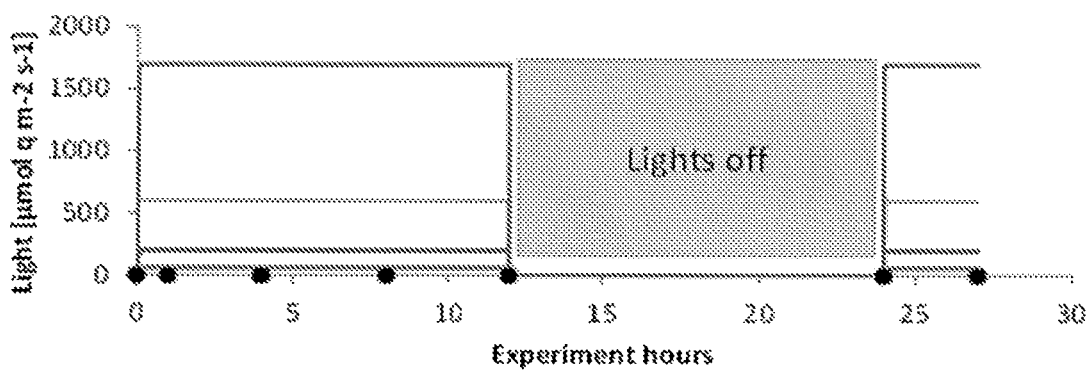
FIG. 2 discloses light doses during light-shift experimental periods and timing of sampling times. Lights were switched off for the night period.

The first example was done using *P. tricornutum* CCAP 1055/1, as it has a high growth rate, it is easy to cultivate and the chlorophyll analysis are reliable. Cells were cultivated in N-replete media using salinity of 6 PSU (8.12 mg $NO_3$—N). Algae was cultivated at 60 µmol q $m^{-2}$ $s^{-1}$ and was kept in the exponential phase by diluting with nutrient replete culture media. Algae concentration was kept low to avoid self-shading. The daily dilutions kept the chlorophyll levels relatively low (around 100-200 µg $L^{-1}$) and thus light conditions inside the cultivation units remained similar throughout the experiment (FIG. 1). With these chlorophyll levels roughly 80-90% of nitrogen is in an inorganic form ($NO_3$) and only 10-20% is taken up in cells. The cultivation volume was gradually increased during the experiment, from 1.8 L in the beginning to 15-17 L in the experimental days. This allowed us to have several units (each 1.5 L) for light shift experiments. Light shift experiments were started at days 12 (exponential growth phase) and at day 17 (stationary growth phase) (FIG. 1). In the experiment, algae culture was divided into several subsamples, which were incubated in different light treatments. Light treatment with duration of 27 hours was conducted using four light levels (60, 200, 600 & 1700 µmol q $m^{-2}$ $s^{-1}$, LED Light Source SL 3500, Photon Systems Instruments), lowest and highest light levels had replicate cultures. In all light experiments lights were switched off for the night (off after the 12 h measurements and switched on sampling for 24 h measurements) (FIG. 2). Cultures were kept in 2 L polycarbonate bottles with continuous aeration (air pump capacity 550 ml/h), which is enough to keep pH and inorganic carbon levels constant when such low biomass is used. High ventilation was used and most of the dissolved oxygen was removed and enough carbon dioxide was incorporated to guarantee that $CO_2$ could not be a growth limiting factor in our trials. Inorganic phosphorus was measured during light-shift experiments, and it was always above 0.4 mg $L^{-1}$, thus in excess for algae growth. The first measuring period was conducted at the exponential phase. The second measuring period took place at the transition to stationary phase, at the onset of nutrient limitation. For this purpose part of the original culture was cultivated at 60 µmol q $m^{-2}$ $s^{-1}$ until $NO_3$ was depleted (FIG. 1).

In the experiment, the amount of cells (flowCAM), lipid accumulation (Nile Red) and photophysiology of the cells (AquaPen) were measured. Photophysiological measurements included light absorption, chl content and photochemical activity using variable fluorescence techniques. The latter was measured using fluorescence-irradiance curve technique (rapid light curves, Suggett et al 2003). For this analysis, subsamples were taken from each culture, as for other analyses, and the fluorescence induction curves were measured using various light levels. From fluorescence response vs. light level curves typical production-photosynthesis parameters were calculated (MacIntyre et al 2002).

Figure 3:
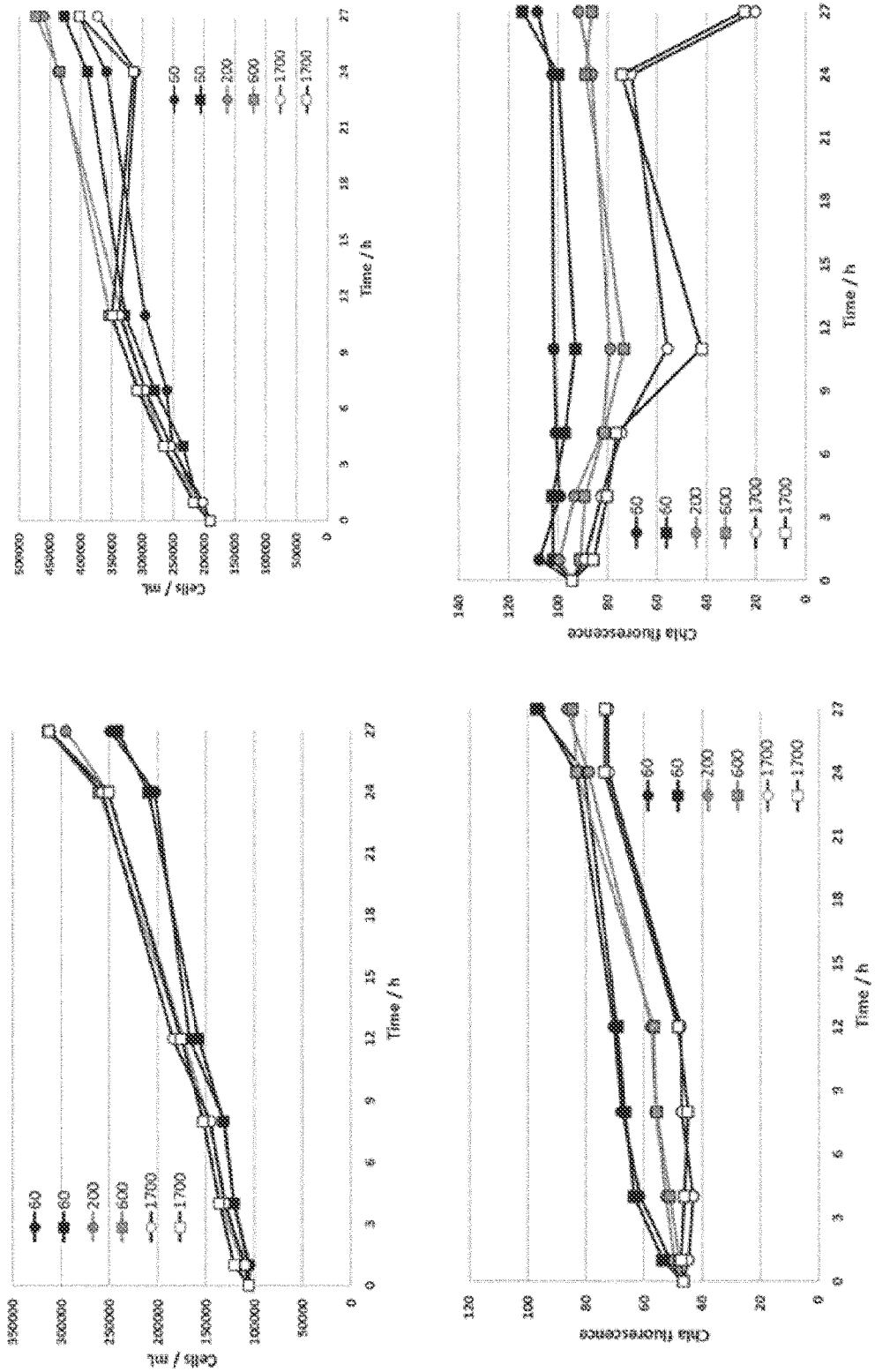
FIG. 3 discloses Light experiment 1. Development of *P. tricornutum* CCAP 1055/1 cell number, Chl (chlorophyll) fluorescence (relative), Nile red fluorescence (relative), cells specific Nile Red fluorescence, photosynthetic efficiency QY (relative), dry weight and nitrate in different light levels in both exponential and stationary growth phases (nitrogen starvation). Note differences in y-scales.
Figure 3:
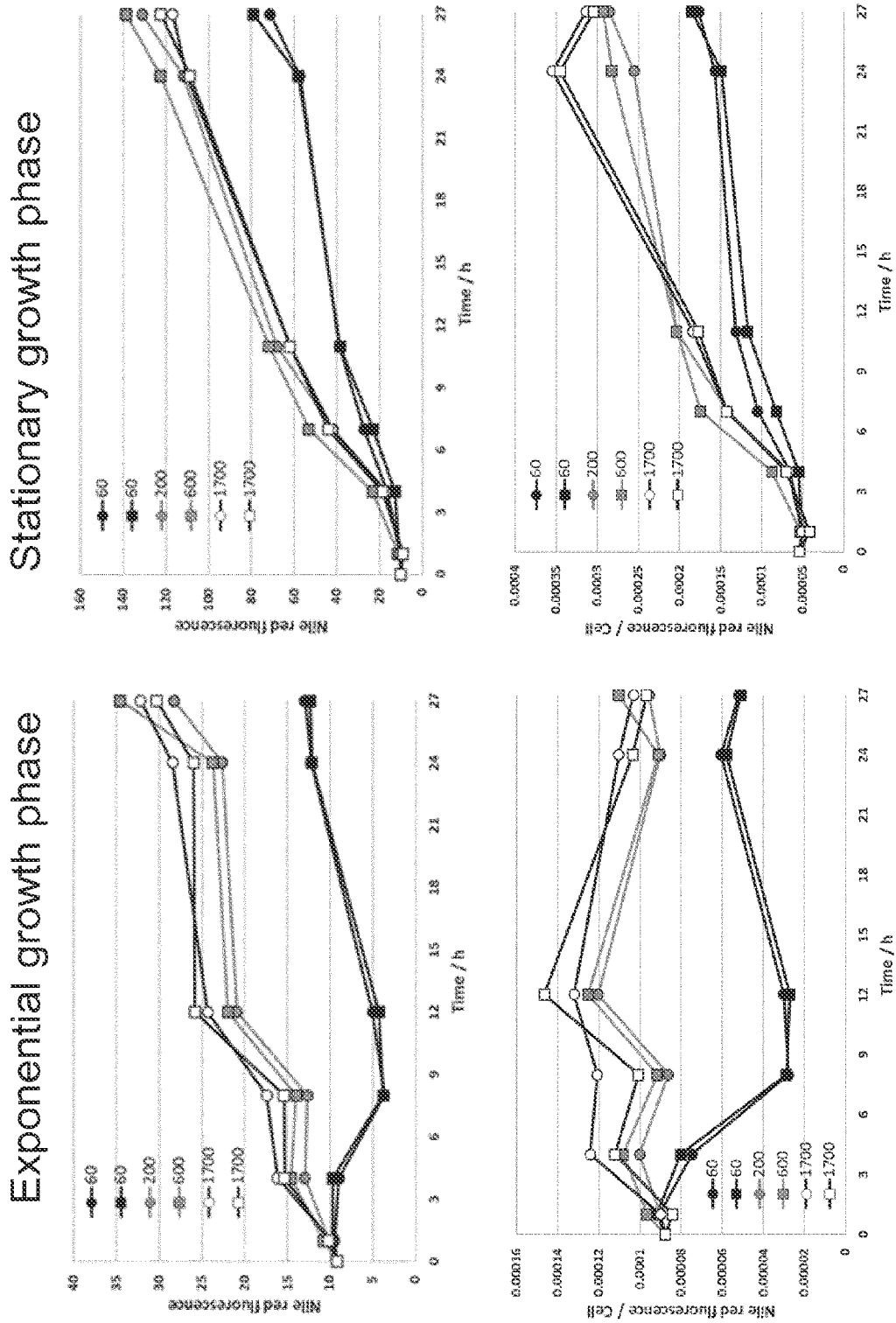
Figure 3:
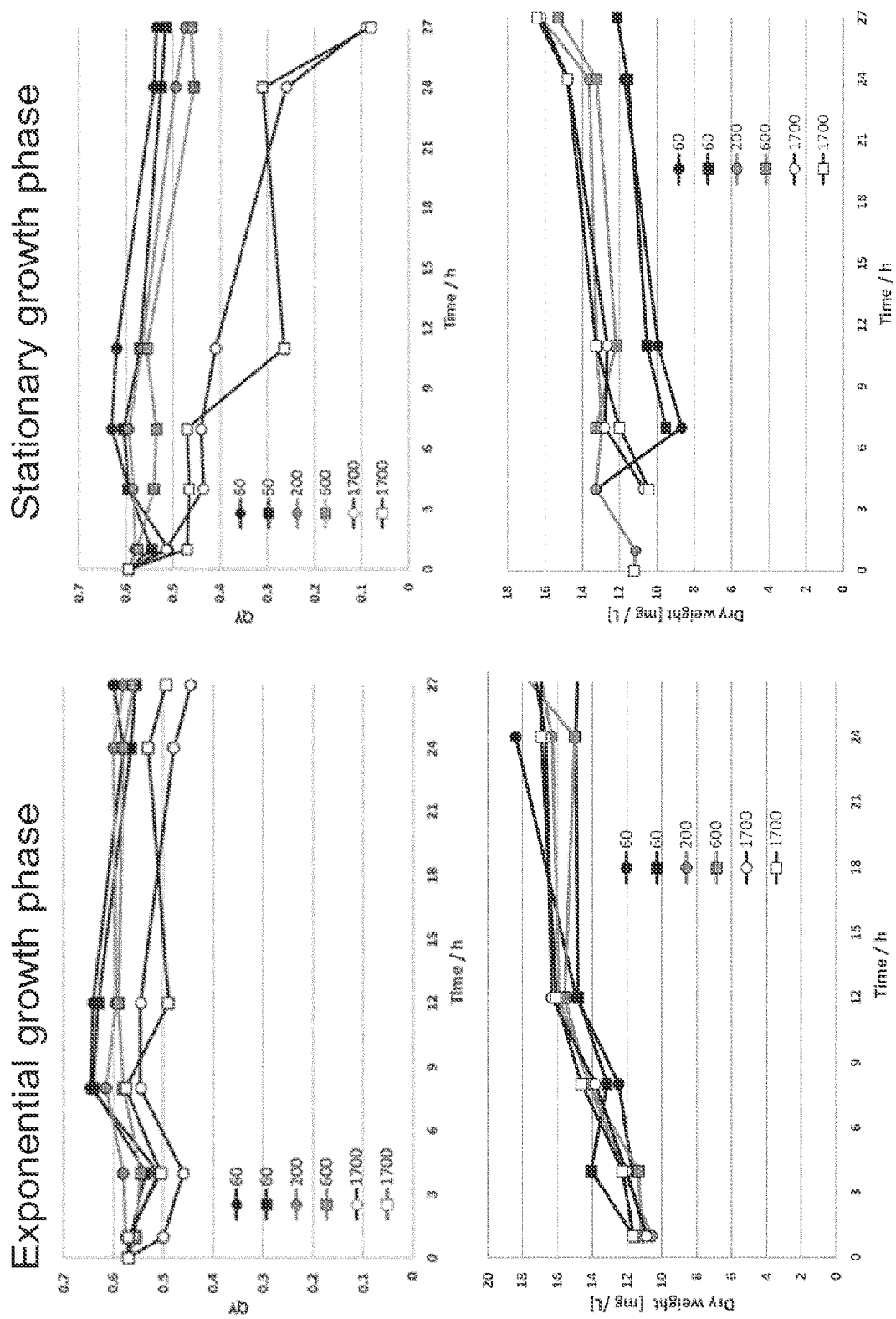
Figure 3:
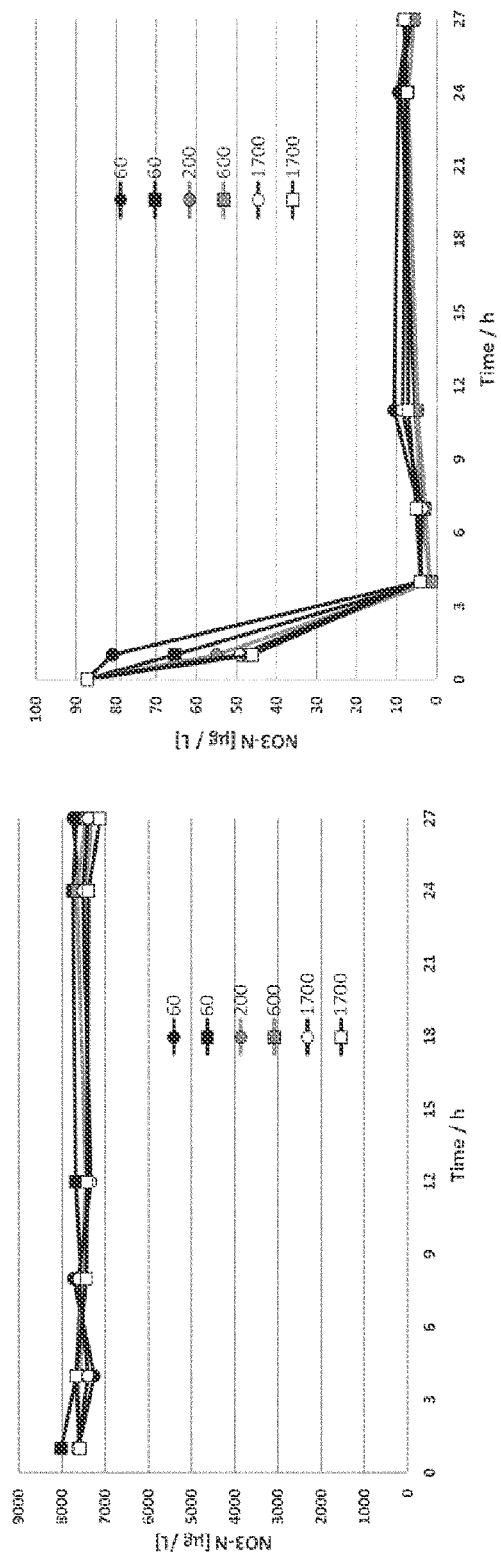
Figure 4:
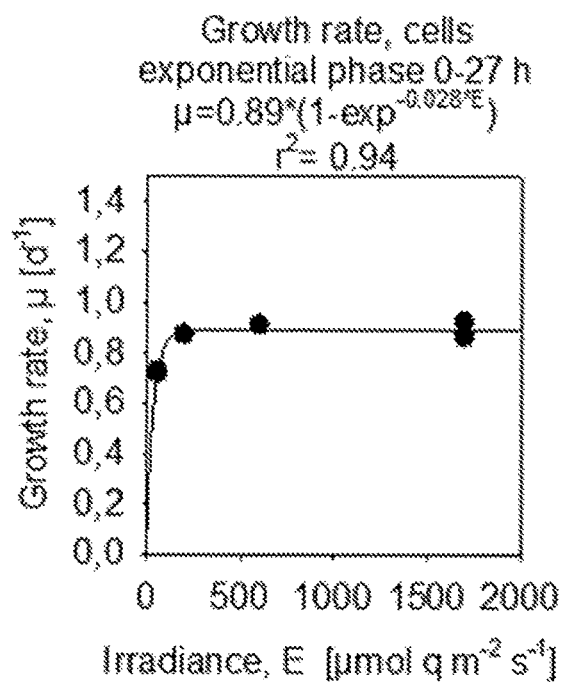
FIG. 4 discloses growth rate for light experiment 1. Upper left: Growth of cell numbers in exponential phase (0-27 hours), Upper right; Growth of cell numbers in stationary phase (0-11 hours), lower left; Growth of lipids (as Nile Red) in exponential phase (0-27 hours), Lower right; Growth of lipids in stationary phase (0-11 hours). Note different y-scale.
Figure 4:
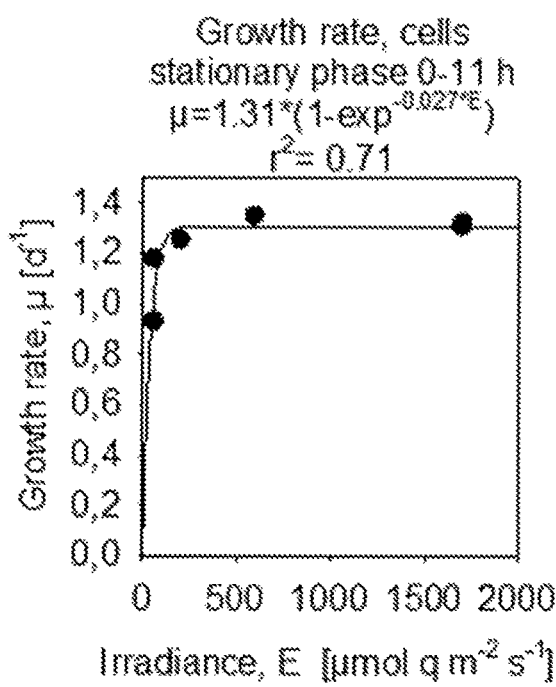
Figure 4:
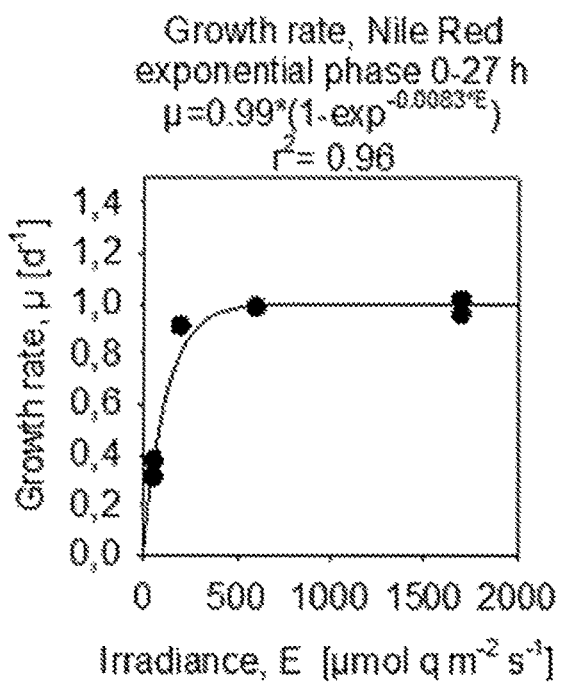
Figure 4:
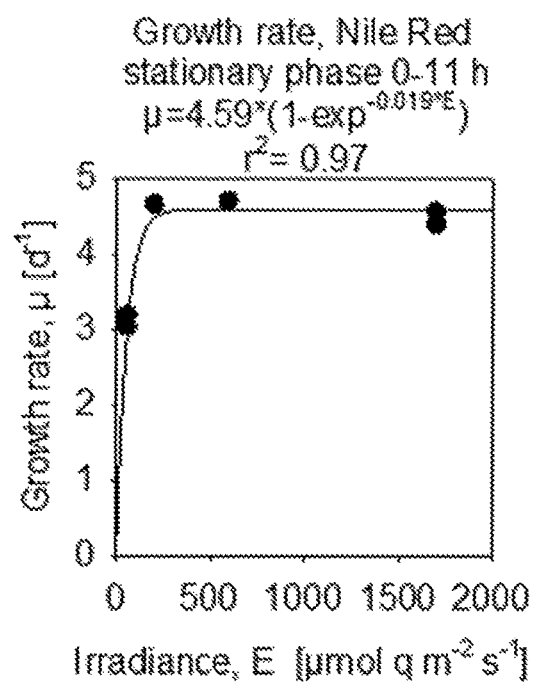
Figure 5:
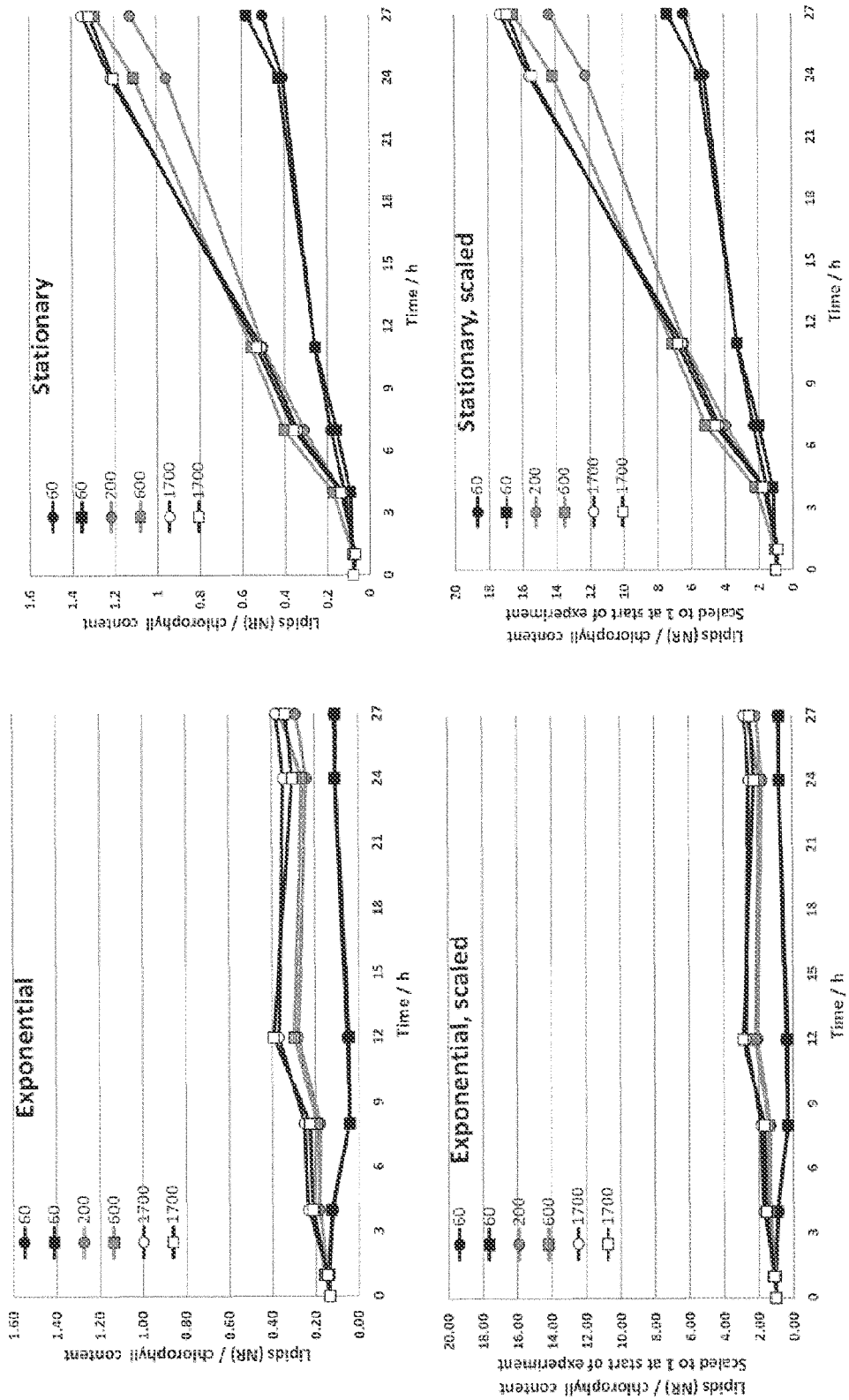
FIG. 5 discloses development of lipid-to-chlorophyll ratio in light experiment during exponential and stationary phases. In lower figures the values have been scaled to 1 at the start of the experiments. The scaled results for the stationary phase show the over 14-17-fold increase in the lipid:chl ratio due to high light treatment.

In the exponential phase light dose affected the growth rate, but clearly the growth was already saturated at 200 µmol q $m^{-2}$ $s^{-1}$ (FIGS. 3 & 4). In lowest light the cell number increased 2.5-fold, while in higher irradiances the increase was 3-fold. Nutrient analyses showed the average nitrate and phosphate concentrations at 7600 and 590 µg $L^{-1}$. These values are very high and during the experimental period hardly any decrease was observed (FIG. 3). Based on variable fluorescence measurements, the cells growing at the highest light level were somewhat stressed by excess light. In that light level Fv/Fm (or QY) values were around 0.50, while other cultures showed values around 0.60, which is typical for unstressed cells (Seppälä 2009). As an acclimation to high light, chlorophyll concentration or fluorescence did not change as much as cell numbers (FIGS. 3 & 5). While cells were dividing faster in high light than in low light, they did not make any new Chlorophyll in high light. This is clearly visible in results of cellular Chlorophyll content, which shows 50% decrease of Chlorophyll content within one day (FIG. 5). Chlorophyll to dry weight ratio (FIG. 5) did not show similar decrease in chlorophyll content, but it must be noted that dry weight measurements were not very reliable, especially for the samples taken at first hours of exponential phase. Part of the excess light energy was used in making up lipids and the lipid content of cells in higher light was 2 times higher than those at 60 µmol q m$^{-2}$ s$^{-1}$ (FIG. 3). When this is coupled with decrease of Chlorophyll content, lipid-to-Chlorophyll ratio increased rapidly and was 2.5-3.5 times higher in saturated irradiance levels, compared to growth irradiance at 60 µmol q m$^{-2}$ s$^{-1}$ (FIG. 3). When looking at the rate of lipid production, much of the differences between cultures seem to be due to decreased production rate of lipids in lowest light (FIG. 4). In other cultures the lipid production rate is slightly higher than the cell growth rate, as seen also in roughly 20-40% increase of their lipid per cell values.

In the onset of stationary phase the cell growth was rather similar in lowest light level than in exponential phase. In higher light levels the growth was even higher than during first part of the experiment. Nutrient results indicated that nitrogen was consumed at the onset of the second part of the experiment and was thus not yet limiting the growth to large extent (FIG. 3). As a first sign of nitrogen limitation, Chlorophyll content was not increasing with the same rate as cell numbers, causing more rapid decrease of cellular Chlorophyll content, even in the lowest light level. Variable fluorescence levels were rather high for the first light period, except for highest light treatment which indicated higher light stress than during exponential growth phase. Highest values are close to the theoretical maximum of 0.65-0.70 which can be obtained in healthy cells (Seppälä 2009). Also Chlorophyll fluorescence dropped in those samples, indicating that fluorescence is decreased by non-photochemical quenching. In highest light, compared to lowest light level, chlorophyll concentration decreased 35% during 24 hours. As the number of cells was rather similar in lowest and highest light levels, in the end of stationary phase experiment, the cell chlorophyll quota also decreased roughly 30% due to high light treatment (FIG. 3).

Lipids started to increase rapidly after nitrogen was depleted. Within 11 hours Nile Red fluorescence was 4-7 fold compared to start of the period (FIG. 3), resulting in much higher production rates than the cell growth rate was (FIG. 4). Together with the decrease of Chlorophyll content, the change in lipid-to-Chlorophyll ratio was even more dramatic. The increase lasted throughout the experiment, and in the end up to 17-fold increase in the ratio was observed (FIG. 5 and Table 1).

In the stationary phase it seems that nutrient stress combined with high light stress decreased the growth, caused large decrease of Chl fluorescence (non-photochemical quenching or photodamage) and decrease of photochemical activity. However, in the lipid increase was equal at all high light cultures. Relative decrease of chlorophyll in cell when grown in high light did not compromise lipid production.

TABLE 1

Relative increase of Nile Red fluorescence and ratio between Nile Red fluorescence and Chlorophyll concentration during the Light experiment 1.

| Irradiance | Time | | | | | | |
|---|---|---|---|---|---|---|---|
| | 0 | 1 | 4 | 8 | 12 | 24 | 27 |
| Exponential Increase of Lipids [Nile red fl] | | | | | | | |
| 60 | 1.00 | 1.03 | 0.97 | 0.40 | 0.54 | 1.32 | 1.40 |
| 60 | 1.00 | 1.06 | 1.05 | 0.41 | 0.46 | 1.31 | 1.34 |
| 200 | 1.00 | 1.10 | 1.40 | 1.37 | 2.27 | 2.46 | 3.06 |
| 600 | 1.00 | 1.17 | 1.58 | 1.52 | 2.38 | 2.57 | 3.75 |
| 1700 | 1.00 | 1.07 | 1.75 | 1.89 | 2.64 | 3.09 | 3.49 |
| 1700 | 1.00 | 1.10 | 1.66 | 1.67 | 2.80 | 2.82 | 3.28 |
| Increase of Lipids vs. Chl [Nile red fl./Chl µgL-1] | | | | | | | |
| 60 | 1.00 | 1.06 | 0.89 | 0.33 | 0.39 | 0.81 | 0.82 |
| 60 | 1.00 | 1.02 | 0.93 | 0.31 | 0.32 | 0.78 | 0.76 |
| 200 | 1.00 | 1.06 | 1.34 | 1.32 | 2.06 | 1.77 | 2.11 |
| 600 | 1.00 | 1.18 | 1.54 | 1.42 | 2.18 | 1.92 | 2.66 |
| 1700 | 1.00 | 1.05 | 1.73 | 1.86 | 2.71 | 2.56 | 2.81 |
| 1700 | 1.00 | 1.09 | 1.58 | 1.67 | 2.88 | 2.24 | 2.48 |
| Stationary Increase of Lipids [Nile red fl] | | | | | | | |
| 60 | 1.00 | 11.02 | 1.63 | 2.67 | 3.80 | 5.61 | 6.96 |
| 60 | 1.00 | 1.06 | 1.26 | 2.26 | 3.76 | 5.68 | 7.73 |
| 200 | 1.00 | 0.93 | 1.79 | 4.10 | 6.65 | 10.93 | 12.82 |
| 600 | 1.00 | 1.11 | 2.29 | 5.20 | 7.02 | 11.98 | 13.56 |
| 1700 | 1.00 | 1.02 | 1.68 | 4.14 | 6.05 | 10.77 | 11.42 |
| 1700 | 1.00 | 0.89 | 1.83 | 4.30 | 6.05 | 10.61 | 11.98 |
| Increase of Lipids vs. Chl [Nile red fl./Chl pgL-1] | | | | | | | |
| 60 | 1.00 | 1.02 | 1.54 | 2.34 | 3.30 | 5.20 | 6.42 |
| 60 | 1.00 | 1.07 | 1.18 | 2.01 | 3.28 | 5.47 | 7.38 |
| 200 | 1.00 | 0.94 | 1.74 | 3.96 | 6.41 | 12.23 | 14.38 |
| 600 | 1.00 | 1.08 | 2.22 | 5.17 | 7.12 | 14.18 | 16.51 |
| 1700 | 1.00 | 0.99 | 1.66 | 4.36 | 6.53 | 15.57 | 17.28 |
| 1700 | 1.00 | 0.89 | 1.77 | 4.58 | 6.79 | 15.40 | 16.86 |

Example 2

The second experiment replicated the first experiment partly, but only light levels 60 and 200 µmol q m$^{-2}$ s$^{-1}$ were used and the measuring period was in the transition to stationary phase only. In addition we tested if the mode of supplying light in different pulses has an effect on lipid accumulation and photophysiology. This was done by applying pulsed light during measuring periods. Pulses were done at sec-min scale (45 sec dim light, 15 sec of high light) or min-hour scales (45 min dim light, 15 min high light). The light levels were dim light=60 µmol q m$^{-2}$ s$^{-1}$ and high light=600 µmol q m$^{-2}$ s$^{-1}$. The accumulated light dose for both pulsed light treatments equal the one with continuous level of 200 µmol q m$^{-2}$ s$^{-1}$.

Figure 6:
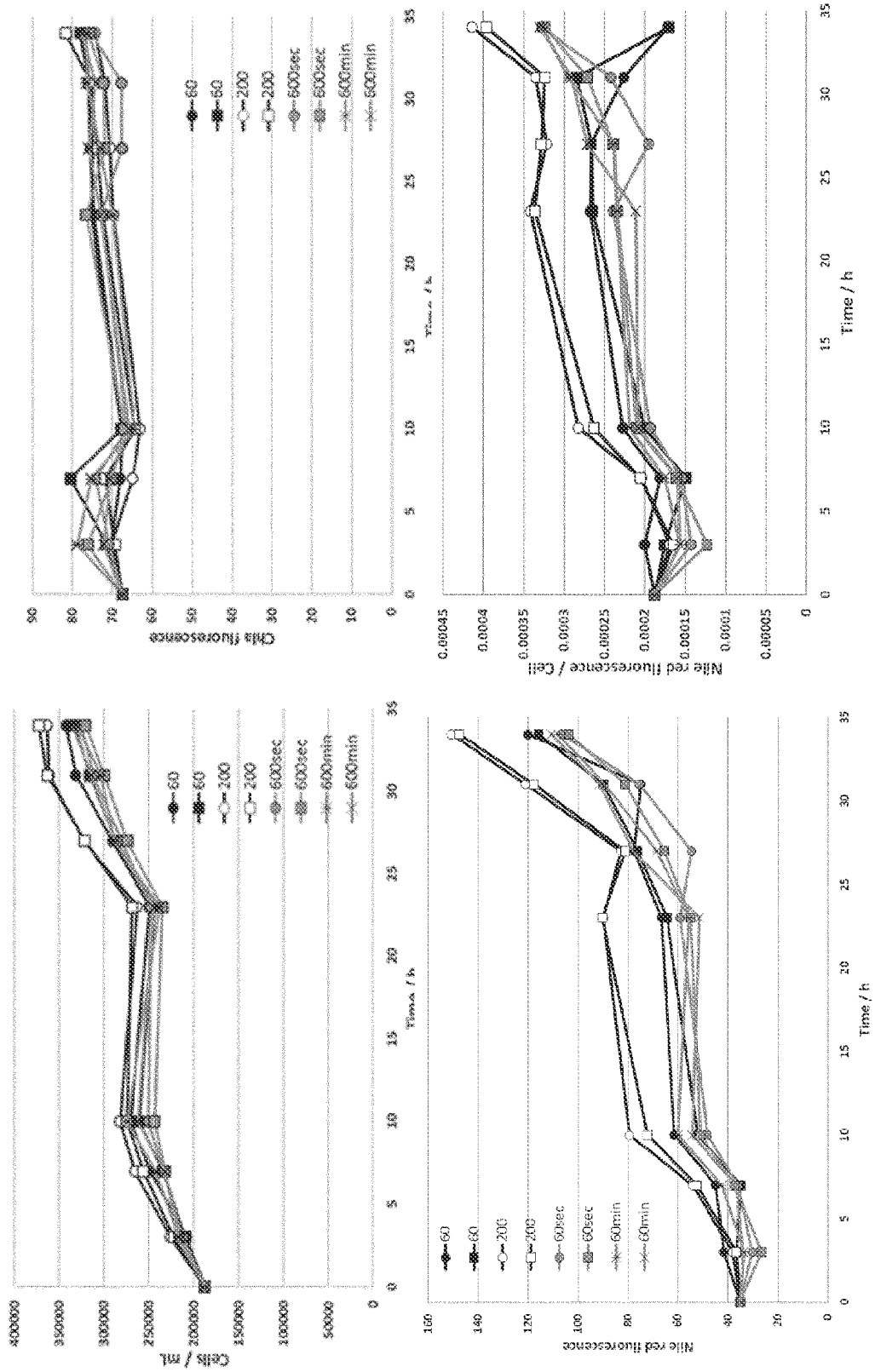
FIG. 6 discloses light experiment 2. Development of *P. tricornutum* CCAP 1055/1 cell number, Chl fluorescence, Nile Red fluorescence, cells specific Nile Red fluorescence, photosynthetic efficiency, lipid (NileRed)—to—chlorophyll concentration ratio, dry weight and nitrate under nitrogen starvation in different light levels/treatments during a time period of 34 h.
Figure 6:
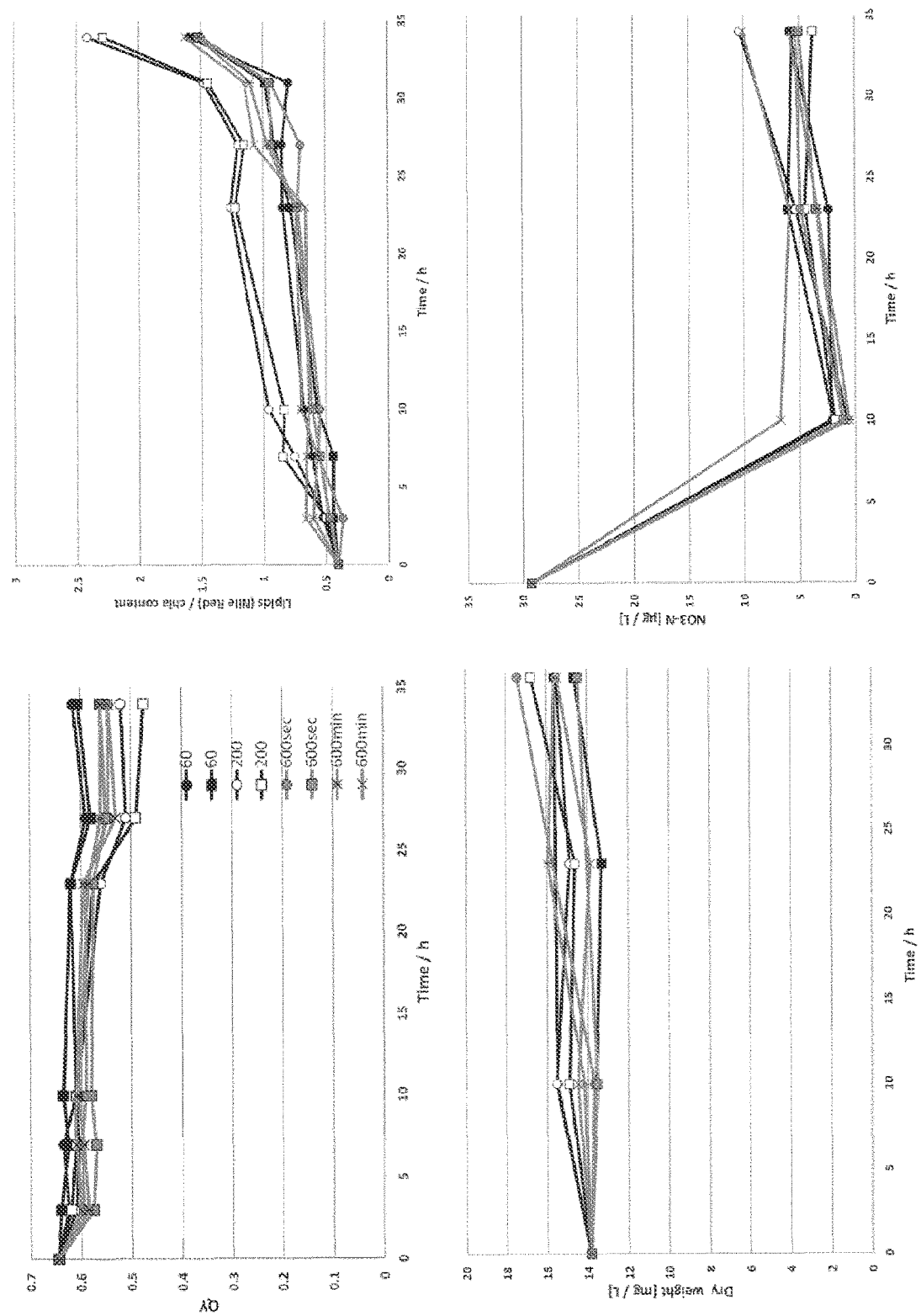

The cell growth was highest at constant light at 200 µmol q m$^{-2}$ s$^{-1}$ (FIG. 6). Similarly, highest lipid yield (absolute, per cell or per chlorophyll) was obtained with this treatment. From the growth curves it seems evident that cells were not able to use the extra energy provided by light pulses. The number of cells was even slightly lower in pulsed light than in low light. Pulsed or especially higher light level decreased photosynthetic efficiency during the experiment.

Figure 7:
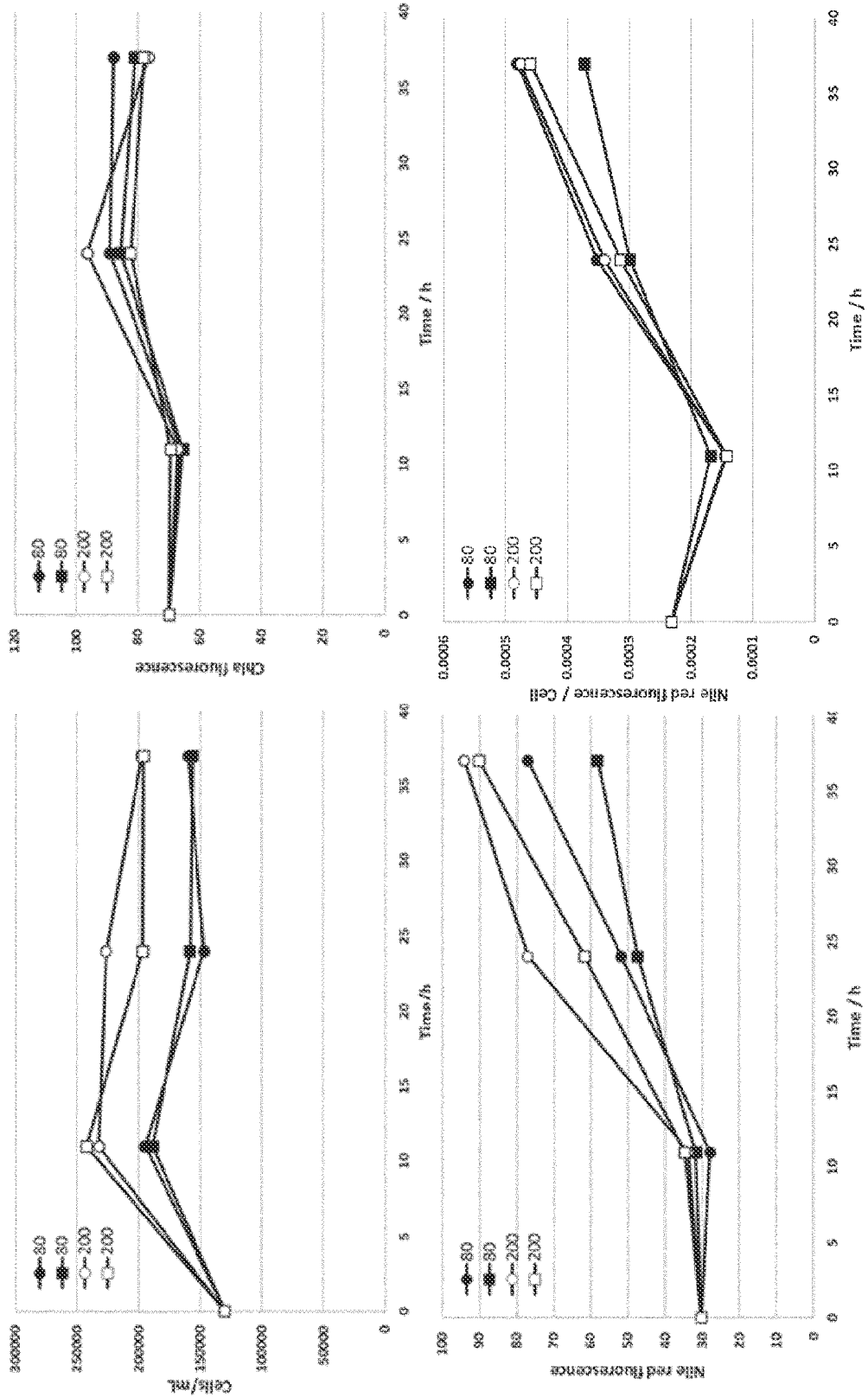
FIG. 7 discloses light experiment 3. Development of *C. vulgaris* cell number, Chl fluorescence, Nile red fluorescence, cells specific Nile Red fluorescence and chlorophyll absorption as indication of chlorophyll concentration, under nitrogen starvation in two different light levels during a time period of 37 h.
Figure 7:
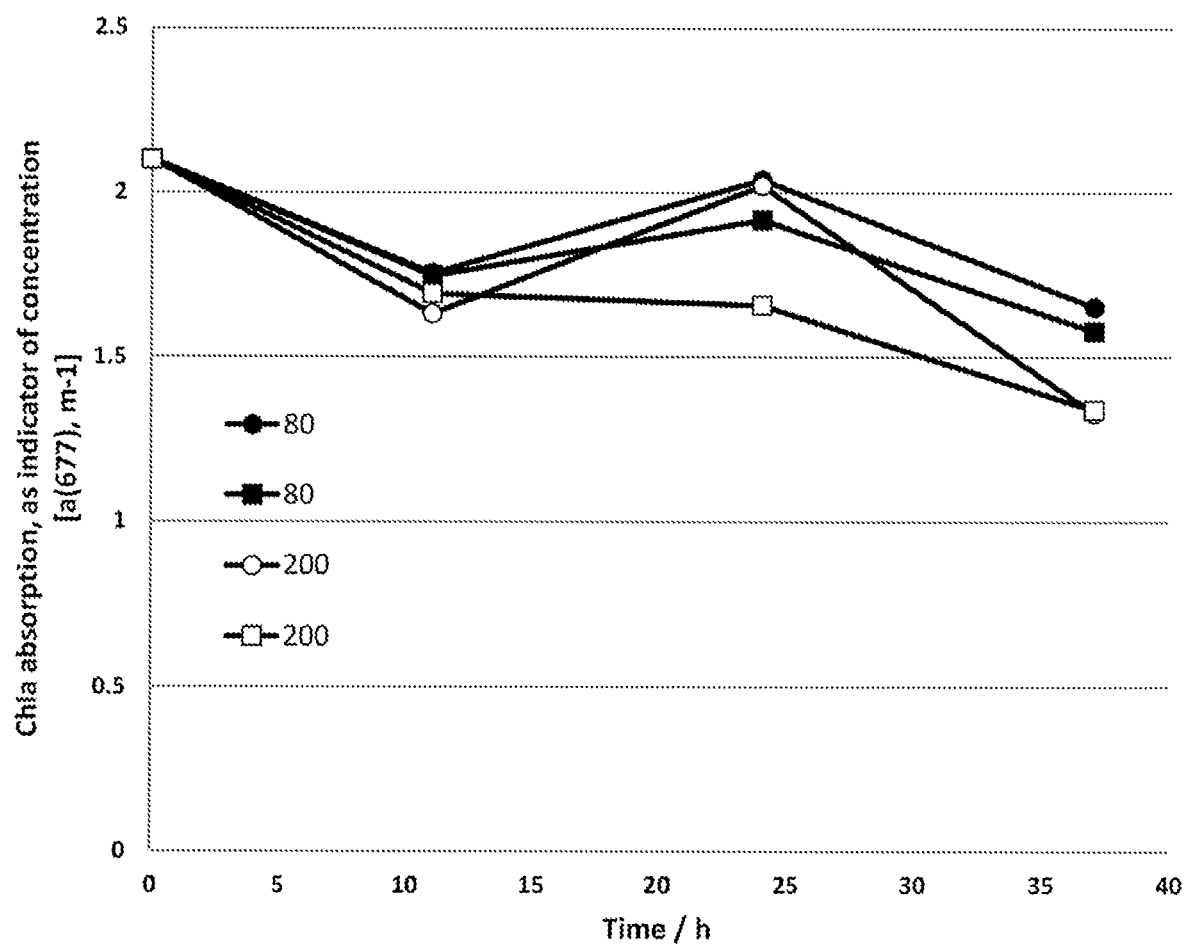

Chlorophyll content of cells (FIG. 7) decreased as in first experiment, but again, pulsed treatments seemed not to influence cell chlorophyll content. The effect of light treatment on spectral absorption was less than in the first experiment. As well, in light-fluorescence relationship the parameters had quite similar ranges in low and high light, and in pulsed light conditions. This indicates very low dynamic light acclimation capacity of cells during this experiment, as during the latter part of the first experiment. The slight differences in pigmentation and lipid content between first and second experiment may be explained by slight shifts in nutrient status of cells. While looking at nitrogen concentrations, similar values observed at the initial stage of second experiment (approx. 30 µg NO$_3$—N L$^{-1}$) are found at 2-3 hours is in the first experiment. As the NO$_3$ uptake may have been low during dark period, the actual difference between developments of nitrogen limitation may be somewhat longer than this time difference. The results indicate that the values at the beginning of second experiment are quite similar to values at 4-11 hours in the first experiment (stationary phase). We may therefore consider that the second experiment shows a case were nutrient limitation has been developed a bit further than in first experiment. This may partly explain why in the second experiment the responses were weaker than in the first experiment; cells were already more nitrogen limited in the second one.

It is likely, from the experimental data collected here, that the time-scale for changes in pigmentation and lipid accumulation is from hours to days, as the shorter minute or second scale light pulses did not cause such strong acclimation.

Example 3

Figure 8:
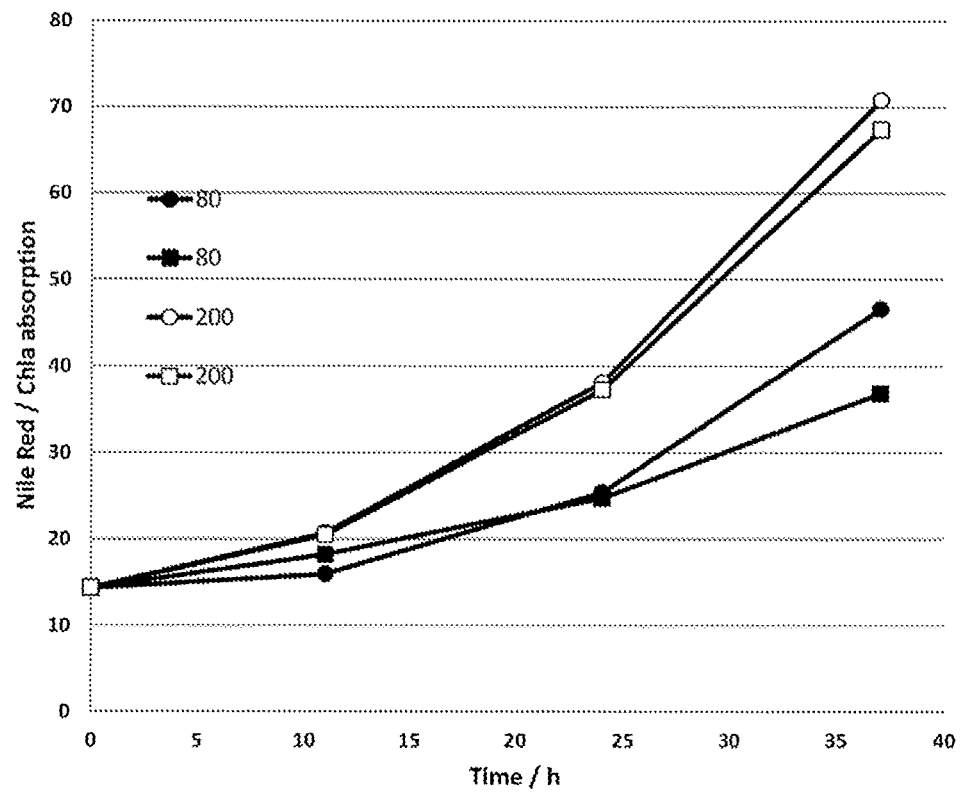
FIG. 8 discloses light experiment 3. Development of lipid-to-chlorophyll ratio in light experiment during transition from exponential to stationary phase.
Figure 8:
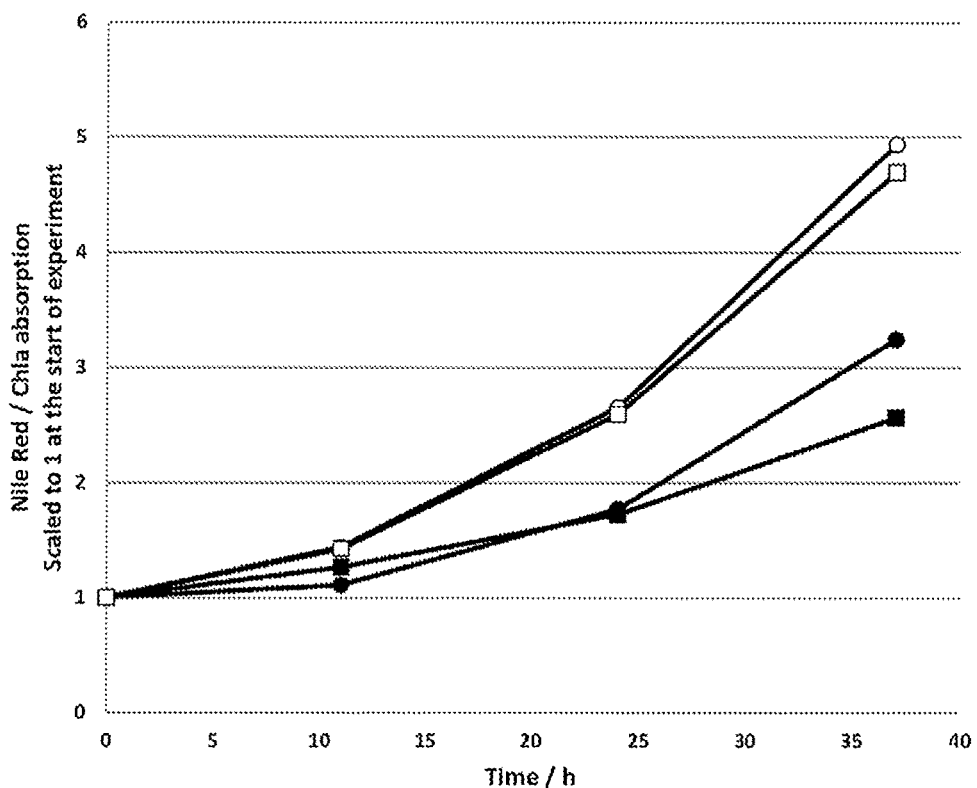

The experiment was carried out using the green algae *Chlorella vulgaris*. Based on the previous experiment, we used only two light treatments, and samples were taken at the beginning and at the end of light periods, for two days. Between experimental hours 11 to 24, the cells were in darkness, while at other times at given irradiances. Like for the previous experiments, cells were first cultivated at lowest irradiance (here, 80 µmol q m$^{-2}$ s$^{-1}$). At the onset from exponential to stationary phase, which is due to nitrogen depletion, the culture was divided into four bottles,

*C. vulgaris* showed high growth, in both cell numbers and in lipids, at high light (FIG. 8). The time of lipid increase took place after cell growth had stopped, after first light period during nitrogen limited conditions. The halt in cell growth was very rapid and the increase in cellular lipids was two-fold. The higher light dosing resulted in somewhat higher lipid-to-chlorofyll ratio. The pigmentation did not respond to the increase of light level, though a slight increase of blue-to-red absorption ratio was noted in the last sample in high light.

The foregoing description has provided, by way of non-limiting examples of particular implementations and embodiments of the invention, a full and informative description of the best mode presently contemplated by the inventors for carrying out the invention. It is however clear to a person skilled in the art that the invention is not restricted to details of the embodiments presented in the foregoing, but that it can be implemented in other embodiments using equivalent means or in different combinations of embodiments without deviating from the characteristics of the invention.

Furthermore, some of the features of the afore-disclosed embodiments of this invention may be used to advantage without the corresponding use of other features. As such, the foregoing description shall be considered as merely illustrative of the principles of the present invention, and not in limitation thereof. Hence, the scope of the invention is only restricted by the appended patent claims.

The invention claimed is:
1. A method of producing algal cells comprising steps of:
   a) cultivating algal cells in culture conditions, using a day-night cycle containing a light period and a dark period and in an amount of light that support growth, and determining the time required for one cell division of the alga in said culture conditions;
   b) depleting the algal cells of at least one inorganic nutrient, wherein the inorganic nutrient contains inorganic nitrogen;
   c) exposing the algal cells continuously during a light period of a day-night light cycle to an amount of light which is higher than in step a) wherein the amount of light has an intensity corresponding to or exceeding a light level of 1.5×E$_k$ of the alga and which is higher than in step a); and
   d) collecting the algal cells after the lipid:chlorophyll ratio has increased at least 3-fold when compared to the lipid:chlorophyll ratio before step c);
   wherein step b) and step c) are started at the same time at a time point that occurs one cell division before and one cell division after the time when the inorganic nutrient is under a detection limit in a culturing medium.

2. The method according to claim 1, wherein the inorganic nutrient in step b) is nitrogen.

3. The method of claim 1, wherein step c) is continued for at least 3 h.

4. The method of claim 1, wherein step b) is started when the algal cells have reached stationary growth phase.

5. The method of claim 1, wherein the algal cells are collected at least 12 h after induction of nutrient depletion.

6. The method of claim 1, wherein step c) is carried out by exposing the alga to an amount of light having an intensity corresponding to or exceeding a light level of 2×Ek of said alga.

7. The method of claim 6, wherein the amount of light has an intensity corresponding to or exceeding a light level of 3×E$_k$ of said alga.

8. The method of claim 2, wherein step c) is continued for at least 3 h.

9. The method of claim 8, wherein step b) is started when the algal cells have reached stationary growth phase.

10. The method of claim 9, wherein the algal cells are collected at least 12 h after induction of nutrient depletion.

11. The method of claim 10, wherein step c) is carried out by exposing the alga to an amount of light having an intensity corresponding to or exceeding a light level of 2×E$_k$ of said alga.

12. The method of claim 1, wherein in step d) the lipid:chlorophyll ratio has increased at least 4-fold when compared to the lipid:chlorophyll ratio before step c).

13. The method of claim 1, wherein in step d) the lipid:chlorophyll ratio has increased between 3-fold and 17-fold when compared to the lipid:chlorophyll ratio before step c).

* * * * *